(12) United States Patent
Bar-Shalom

(10) Patent No.: US 9,937,295 B2
(45) Date of Patent: Apr. 10, 2018

(54) SYRINGE FOR MIXING AND EJECTING AN ACTIVE PHARMACEUTICAL INGREDIENT

(75) Inventor: Daniel Bar-Shalom, Kokkedal (DK)

(73) Assignee: BIONEER A/S, Horsholm (DK)

( * ) Notice: Subject to any disclaimer, the term of this patent is extended or adjusted under 35 U.S.C. 154(b) by 684 days.

(21) Appl. No.: 13/982,844

(22) PCT Filed: Feb. 2, 2012

(86) PCT No.: PCT/EP2012/051759
§ 371 (c)(1),
(2), (4) Date: May 6, 2014

(87) PCT Pub. No.: WO2012/104376
PCT Pub. Date: Aug. 9, 2012

(65) Prior Publication Data
US 2014/0236121 A1    Aug. 21, 2014

Related U.S. Application Data

(60) Provisional application No. 61/438,661, filed on Feb. 2, 2011.

(51) Int. Cl.
*A61M 5/19*    (2006.01)
*A61M 5/315*    (2006.01)

(52) U.S. Cl.
CPC .......... *A61M 5/31596* (2013.01); *A61M 5/19* (2013.01); *A61M 5/31511* (2013.01); *A61M 2005/31598* (2013.01)

(58) Field of Classification Search
CPC ..................... B01F 13/00; A61M 1/00; A61M 2005/31598; A61M 5/31596; A61M 5/19;
(Continued)

(56) References Cited

U.S. PATENT DOCUMENTS 2,708,438 A * 5/1955 Cohen .................. A61M 5/284
604/192
3,718,139 A * 2/1973 Hanford ............ A61M 5/31596
604/87

(Continued)

FOREIGN PATENT DOCUMENTS

WO    WO 92/10225 A1    6/1992
WO    WO 2004/026377 A1    4/2004

OTHER PUBLICATIONS

Colin W. Pouton, Formulation of self-emulsifying drug delivery systems, 1997, Elsevier Science B.V., 25th Edition, pp. 47-58.*
Office Action for Japanese Patent Application No. 2013-552203 dated Feb. 9, 2016.
International Search Report and Written Opinion for corresponding International Application No. PCT/EP2012/051759 dated May 7, 2012.

*Primary Examiner* — Nathan R Price
*Assistant Examiner* — John Doubrava
(74) *Attorney, Agent, or Firm* — Alston & Bird LLP

(57) ABSTRACT

A syringe (1) for mixing and ejecting an active pharmaceutical ingredient is disclosed. The syringe (1) comprises a syringe body (2) defining a first lumen (8), a first plunger (4) arranged movably in said first lumen (8), said first plunger (4) being hollow, thereby defining a second lumen (9) being separated from the first lumen (8), and a second plunger (5) arranged movably in said second lumen (9). A liquid diluent is contained in one of the first lumen (8) and the second lumen (9), and an active pharmaceutical ingredient is contained in the other of the first lumen (8) and the second lumen (9). The second plunger (5) is movable in such a manner that the active pharmaceutical ingredient and the liquid diluent are brought together, e.g. in the first lumen (8) or in the second lumen (9), thereby causing the active pharmaceutical ingredient to be diluted by the diluent, and (Continued)

the first plunger (4) and/or the second plunger (5) is/are movable in such a manner that diluted active pharmaceutical ingredient can be ejected from the syringe (1). The syringe (1) provides a single device for mixing and ejecting the active pharmaceutical ingredient. This reduces the risk of contamination, and the syringe (1) can be easily operated by an untrained user.

20 Claims, 8 Drawing Sheets

(58) Field of Classification Search
CPC .............. A61M 5/31511; A61M 3/005; A61M 5/2066; A61M 5/2448; A61M 5/284; A61M 5/3294; A61J 1/2093; A61J 1/2089; A61J 1/2096
See application file for complete search history.

(56) References Cited

U.S. PATENT DOCUMENTS

| | | | | |
|---|---|---|---|---|
| 4,405,317 | A * | 9/1983 | Case | A61M 5/31596 604/90 |
| 5,429,603 | A * | 7/1995 | Morris | A61M 5/3145 604/87 |
| 7,018,089 | B2 * | 3/2006 | Wenz | A61M 5/31511 206/219 |
| 2004/0122359 | A1 | 6/2004 | Wenz et al. | |
| 2012/0259279 | A1 * | 10/2012 | Finke | A61M 5/31596 604/87 |

* cited by examiner

US 9,937,295 B2

SYRINGE FOR MIXING AND EJECTING AN ACTIVE PHARMACEUTICAL INGREDIENT

CROSS-REFERENCE TO RELATED APPLICATIONS

This application is the U.S. National Stage of International Application PCT/EP2012/051759 filed Feb. 2, 2012, which designates the U.S. and was published by the International Bureau in English on Aug. 9, 2012, and which claims the benefit of U.S. Provisional Application No. 61/438,661, filed Feb. 2, 2011, all of which are hereby incorporated by reference in their entirety.

FIELD OF THE INVENTION

The present invention relates to a syringe for delivering drugs. The syringe of the invention can be used for mixing an active pharmaceutical ingredient in a dry form or in the form of a solution with a diluent, prior to delivery of the mixed drug. The present invention further relates to a method of mixing and ejecting an active pharmaceutical ingredient, using such a syringe.

BACKGROUND OF THE INVENTION

Previously, active pharmaceutical ingredient and diluent had to be provided in separate containers, and the contents of the separate containers needed to be brought together, e.g. in a vial or a syringe, in order to mix the contents prior to delivering the mixed drug. Thus, in prior art systems, the diluent, the active pharmaceutical ingredient and the mixing volume need to be kept under sterile conditions. Furthermore there is a risk that the active pharmaceutical ingredient and the diluent are not properly mixed.

DESCRIPTION OF THE INVENTION

It is an object of embodiments of the invention to provide a syringe in which mixing and ejection of an active pharmaceutical ingredient can be easily handled.

It is a further object of embodiments of the invention to provide a syringe in which the risk of contamination is minimised.

It is an even further object of embodiments of the invention to provide a method for mixing and ejecting an active pharmaceutical ingredient, which can easily be performed by an untrained user.

According to a first aspect the invention provides a syringe comprising:
 a syringe body defining a first lumen,
 a first plunger arranged movably in said first lumen, said first plunger being hollow, thereby defining a second lumen being separated from the first lumen, and
 a second plunger arranged movably in said second lumen,
 wherein a liquid diluent is contained in one of the first lumen and the second lumen, and an active pharmaceutical ingredient is contained in the other of the first lumen and the second lumen, wherein the second plunger is movable in such a manner that the active pharmaceutical ingredient and the liquid diluent are brought together, thereby causing the active pharmaceutical ingredient to be diluted by the diluent, and wherein the first plunger and/or the second plunger is/are movable in such a manner that diluted active pharmaceutical ingredient can be ejected from the syringe.

In the present context the term 'syringe' should be interpreted to mean a device which can be used for delivering or ejecting a liquid drug, preferably via a needle attached to or forming part of the syringe.

In the present context the term 'plunger' should be interpreted to mean a part which is movable along a substantially axial direction of the syringe.

In the present context the term 'lumen' should be interpreted to mean a cavity capable of accommodating one or more parts of the syringe and/or liquid or solid material to be delivered from the syringe.

The liquid diluent is contained either in the first lumen or in the second lumen. In the case that the liquid diluent is contained in the first lumen, the active pharmaceutical ingredient is contained in the second lumen. Similarly, in the case that the liquid diluent is contained in the second lumen, the active pharmaceutical ingredient is contained in the first lumen. Thus, the liquid diluent and the pharmaceutical ingredient are not contained in the same lumen during storage of the syringe.

The second lumen is separated from the first lumen. It should be noted that this ensures that the active pharmaceutical ingredient is kept separate from the diluent during storage of the syringe. However, it is not ruled out that the first lumen and the second lumen are brought together or that a fluid connection is established between the first lumen and the second lumen during operation of the syringe. This will be described further below.

As will be described in further detail below, the syringe can be operated to mix the active pharmaceutical ingredient and the diluent to form the final mixed drug. Subsequently, the mixed drug can be ejected directly from the syringe. Thus, every element/part/component required for providing the final drug is contained in the syringe, which is thereby delivered as a single unit. The syringe is easy to operate, and the risk of introducing errors or contamination during mixing and delivery of the drug is minimised.

The second plunger may carry the active pharmaceutical ingredient or the liquid diluent. In the case that the second plunger carries the active pharmaceutical ingredient then the active pharmaceutical ingredient is contained in the second lumen and the diluent is contained in the first lumen. Similarly, in the case that the second plunger carries the diluent, then the diluent is contained in the second lumen and the active pharmaceutical ingredient is contained in the first lumen.

According to this embodiment, the second plunger may be movable in such a manner that the active pharmaceutical ingredient or the liquid diluent carried by the second plunger is moved into the first lumen. Thereby the diluent and the active pharmaceutical ingredient are brought together in the first lumen.

The second plunger may comprise a first part adapted to carry the active pharmaceutical ingredient or the liquid diluent, and a second part comprising a portion being operable by a user, and the first part and the second part may be manufactured as separate parts and attached to each other during assembly of the syringe. According to this embodiment, the first part and the second part of the second plunger are initially manufactured as separate parts. During assembly of the syringe, the first part of the second plunger may be mounted in the second lumen inside the first plunger, and then the active pharmaceutical ingredient or the liquid diluent may be arranged on the first part of the second plunger. Finally, the second part of the second plunger is attached to the first part of the second plunger. As an alternative, the active pharmaceutical ingredient or the liquid diluent may be arranged on the first part of the second plunger before the first part of the second plunger is mounted in the second lumen inside the first plunger.

The second part of second plunger may have a cross sectional diameter which is larger than a cross sectional diameter of the first part of the second plunger. According to this embodiment, the active pharmaceutical ingredient or the liquid diluent may be accommodated in the space defined inside the second lumen between the smaller cross sectional diameter of the first part of the second plunger and an inner wall of the first plunger.

The embodiment described above is particularly advantageous in the case that the second plunger carries the active pharmaceutical ingredient, and the active pharmaceutical ingredient is in the form of a lyophilized drug prior to bringing the active pharmaceutical ingredient and the liquid diluent together. In this case, the first part of the second plunger may be mounted in the second lumen inside the first plunger. Then a substance containing the active pharmaceutical ingredient is applied to the second lumen. The first plunger, including the first part of the second plunger and the substance containing the active pharmaceutical ingredient, is then arranged in a normal lyophilisation machine, where lyophilisation of the active pharmaceutical ingredient takes place. Thereby it is obtained that the active pharmaceutical ingredient is lyophilized directly onto the first part of the second plunger, and this is obtained using normal lyophilisation techniques and equipment. Once the lyophilisation has been completed, the second part of the second plunger is attached to the first part of the second plunger.

Thus, the second plunger may be movable in such a manner that the active pharmaceutical ingredient and the liquid diluent are brought together in the first lumen. This may, e.g., be obtained in the manner described above. As an alternative, it may be obtained by pushing diluent from the second lumen into the first lumen, containing the active pharmaceutical ingredient, by means of the second plunger, e.g. through a membrane separating the first lumen from the second lumen. In this case the membrane may be designed in such a manner that it breaks when subjected to a pressure, thereby allowing the diluent to flow into the first lumen. When the mixed drug is subsequently ejected from the syringe, it is ejected from the first lumen by moving the first plunger.

As another alternative, the diluent and the active pharmaceutical ingredient may be brought together in the second lumen. This may, e.g., be obtained by sucking diluent from the first lumen into the second lumen by moving the second plunger in a direction away from the first lumen. The diluent may, e.g., flow through a membrane separating the first lumen from the second lumen, in the manner described above. In this case the pressure in the first lumen will decrease as the diluent is sucked into the second lumen. This will move the first plunger, thereby decreasing the volume of the first lumen. When all of the diluent has been moved to the second lumen, the volume of the first lumen may have decreased to essentially zero. When the mixed drug is subsequently ejected from the syringe, it is ejected directly from the second lumen by moving the second plunger.

The syringe body, the first plunger and the second plunger may be arranged substantially coaxially. In this case the plungers are preferably moved along the common axis during operation of the syringe. As an alternative, the first plunger may be arranged eccentrically relative to the syringe body and/or the second plunger may be arranged eccentrically relative to the first plunger.

According to one embodiment, at least part of the second plunger can be removed from the syringe. The removable part may, e.g., be a part which is pushed by the operator when the second plunger is operated to bring the active pharmaceutical ingredient and the diluent together. This is particularly an advantage in the case that the first plunger is operated in order to eject the mixed drug from the syringe. In this case, removal of this part of the second plunger ensures that it is not in the way when the first plunger is subsequently pushed in order to eject the mixed drug from the syringe. The part may, e.g., be removed by breaking it off. The remaining part of the second plunger, e.g. a part carrying the active pharmaceutical ingredient or the diluent, may, in this case, advantageously be immobilised, at least in a direction transversely to an axial direction of the syringe, with respect to the syringe body and/or with respect to the first plunger in order to ensure that it is not allowed to move freely inside the first lumen.

Alternatively or additionally, the syringe may further comprise a removable locking member, said locking member being adapted to prevent movements of the second plunger relative to the first plunger when the locking member is mounted on the syringe, and wherein the second plunger is allowed to perform movements relative to the first plunger when the locking member is removed from the syringe. According to this embodiment, the locking member ensures that the second plunger is not moved relative to the first plunger when it is intended to move the first plunger in order to eject the mixed drug from the syringe. Thus, the second plunger is moved along with the first plunger. This allows the ejecting process to be handled in an accurate manner. Furthermore, since the locking member is removable, the second plunger is allowed to perform the required movements during the mixing process. This is obtained simply by removing the locking member.

A syringe according to the embodiment described above may, e.g., be operated in the following manner. During storage the locking member is mounted on the syringe. Thereby it is prevented that the second plunger is accidentally moved during storage, and it is thereby ensured that the active pharmaceutical ingredient and the diluent are kept separately during storage. When it is intended to mix and eject the drug, a user removes the locking member, thereby allowing movements of the second plunger. Then the user operates the second plunger in order to bring the active pharmaceutical ingredient and the diluent together, thereby causing the active pharmaceutical ingredient and the diluent to mix and form the diluted pharmaceutical ingredient. When the mixing has been completed, the locking member is once again mounted on the syringe, thereby preventing further movements of the second plunger relative to the first plunger. This allows the first plunger to be operated in order to eject the diluted active pharmaceutical ingredient from the syringe, while ensuring that the second plunger is not simultaneously moved relative to the first plunger.

A perforated disk may be mounted on the second plunger, said perforated disk being arranged in the first lumen in such a manner that a part of the second plunger is allowed to be moved back and forth inside the first lumen. According to this embodiment, the second plunger can be moved back and forth in the diluent contained in the first lumen. In the case that the diluent and the active pharmaceutical ingredient are brought together in the first lumen, such a movement causes turbulence in the diluent, thereby ensuring proper mixing of the active pharmaceutical ingredient and the diluent. In the case that the second plunger carries the active pharmaceutical ingredient, the part of the second plunger which is allowed to be moved back and forth inside the first lumen may advantageously be the part which carries the active pharmaceutical ingredient. Thereby the active pharmaceutical ingredient is also moved back and forth in the first lumen containing the diluent, and thereby proper mixing is ensured.

The active pharmaceutical ingredient may be in a dry form prior to bringing the active pharmaceutical ingredient and the liquid diluent together. In this case the active pharmaceutical ingredient may, e.g., be in the form of a powder, a pellet or a tablet. Alternatively, the active pharmaceutical ingredient may be lyophilized directly onto a part of the syringe, e.g. onto the second plunger or a wall part of the first lumen or the second lumen.

As an alternative, the active pharmaceutical ingredient may be in the form of a solution or a suspension prior to bringing the active pharmaceutical ingredient and the liquid diluent together. In this case the diluent may be in the form of self-emulsifying oil.

At least a part of the second plunger may be deformable. In particular, a part of the second plunger which carries the active pharmaceutical ingredient may be deformable. The active pharmaceutical ingredient may be carried in a cavity formed in the second plunger. There is a risk that mixed drug is caught in such a cavity, in which case the amount of drug delivered from the syringe is smaller than it is supposed to be. By compressing or deforming this part of the second plunger, e.g. during ejection of the mixed drug, such a cavity is collapsed, and it is thereby ensured that all of the mixed drug is in fact delivered from the syringe.

According to a second aspect the invention provides a method for mixing and ejecting an active pharmaceutical ingredient from a syringe, the syringe comprising a syringe body, a first plunger arranged movably inside a first lumen defined by the syringe body and a second plunger arranged movably inside a second lumen defined by the first plunger, a liquid diluent being contained in one of the first lumen and the second lumen, and an active pharmaceutical ingredient being contained in the other of the first lumen and the second lumen, the method comprising the steps of:

moving the second plunger, thereby bringing the active pharmaceutical ingredient and the liquid diluent together, mixing the active pharmaceutical ingredient and the liquid diluent, thereby obtaining a diluted active pharmaceutical ingredient, and moving the first plunger and/or the second plunger in such a manner that the diluted active pharmaceutical ingredient is ejected from the syringe.

It should be noted that a person skilled in the art would readily recognise that any feature described in combination with the first aspect of the invention could also be combined with the second aspect of the invention, and vice versa.

The second aspect of the invention relates to a method for mixing and ejecting an active pharmaceutical ingredient from a syringe. The syringe may advantageously be a syringe according to the first aspect of the invention, and the remarks set forth above are therefore also applicable here.

During storage the active pharmaceutical ingredient and the liquid diluent are kept separately in the syringe, as described above with reference to the first aspect of the invention. When it is desired to mix and eject an active pharmaceutical ingredient from the syringe, the second plunger is initially operated in such a manner that the active pharmaceutical ingredient and the liquid diluent are brought together, e.g. in the first lumen or in the second lumen.

Then the active pharmaceutical ingredient and the liquid diluent are mixed. This may, e.g., be done simply by waiting until the active pharmaceutical ingredient is sufficiently diluted or solved. Alternatively, it may be obtained by moving the second plunger back and forth inside the first lumen as described above.

Then the first plunger and/or the second plunger is/are operated in such a manner that the diluted active pharmaceutical ingredient is ejected from the syringe, e.g. via a needle which is mounted on or forms part of the syringe. In the case that the active pharmaceutical ingredient and the liquid diluent are brought together in the first lumen, the first plunger may advantageously be operated in order to eject the diluted active pharmaceutical ingredient from the syringe, since the first plunger is movable inside the first lumen, and is therefore suitable for causing ejection of liquid from the first lumen. Similarly, in the case that the active pharmaceutical ingredient and the liquid diluent are brought together in the second lumen, the second plunger may advantageously be operated in order to eject the diluted active pharmaceutical ingredient from the syringe, since the second plunger is movable inside the second lumen, and is therefore suitable for causing ejection of liquid from the second lumen. As an alternative, ejection of the diluted pharmaceutical ingredient from the syringe may be caused by combined movements of the first plunger and the second plunger.

In the method according to the second aspect of the invention, the active pharmaceutical ingredient and the liquid diluent are mixed in and ejected from a single unit. This makes it easy for a user to mix and administer the drug, and the risk of contamination of the drug is minimised.

The step of moving the second plunger may bring the active pharmaceutical ingredient and the liquid diluent together in the first lumen, and the step of mixing the active pharmaceutical ingredient and the liquid diluent may comprise moving the second plunger back and forth inside the first lumen. The back and forth movement of the second plunger inside the first lumen ensures proper mixing of the active pharmaceutical ingredient and the liquid diluent, as described above.

The method may further comprise the step of locking the second plunger against movements relative to the first plunger, said step being performed after the step of mixing the active pharmaceutical ingredient and the liquid diluent and before the step of moving the first plunger and/or the second plunger. As described above, this ensures that the first plunger can be moved in order to cause ejection of the diluted active pharmaceutical ingredient, while ensuring that the second plunger is not moved relative to the first plunger.

The step of locking the second plunger may be performed by mounting a locking member on the syringe, as described above. As an alternative, the step of locking the second plunger may be performed by removing at least a part of the second plunger from the syringe. This has also been described above.

In the case that the step of locking the second plunger is performed by mounting a locking member on the syringe, the locking member may be mounted on the syringe during storage, and the method may further comprise the step of removing the locking member prior to moving the second plunger. As described above, it is thereby prevented that the active pharmaceutical ingredient and the liquid diluent are accidentally brought together during storage.

BRIEF DESCRIPTION OF THE DRAWINGS

The invention will now be described in further detail with reference to the accompanying drawings in which.

DETAILED DESCRIPTION OF THE DRAWINGS

Figure 1:
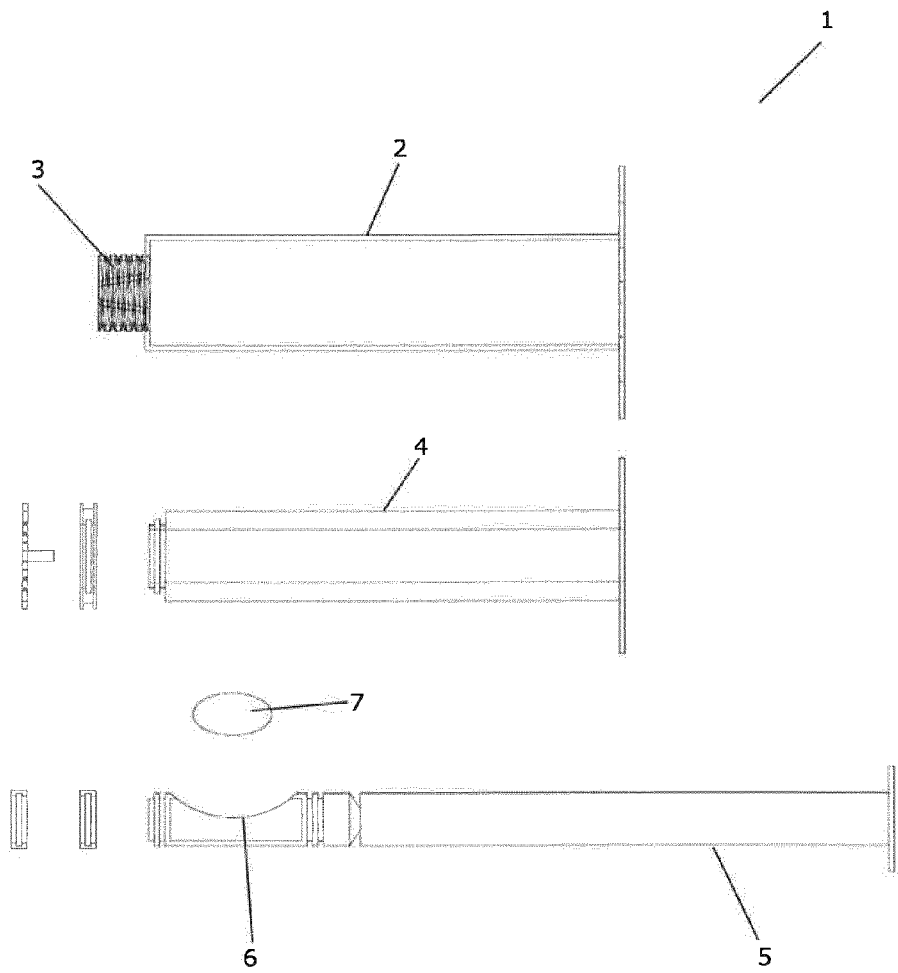
FIG. 1 is an exploded view of a syringe according to a first embodiment of the invention.

FIG. 1 is an exploded view of a syringe 1 according to an embodiment of the invention. Thus, FIG. 1 shows a syringe body 2 provided with a threaded end 3 for attaching a needle, a first plunger 4 and a second plunger 5. The second plunger 5 is provided with a cavity 6 for carrying a pellet 7 comprising an active pharmaceutical ingredient. When the syringe 1 is assembled, the second plunger 5 is introduced into the first plunger 4 which is in turn introduced into the syringe body 2. A diluent is arranged in a lumen defined inside the syringe body 2 and delimited by the first plunger 4.

Figure 2:
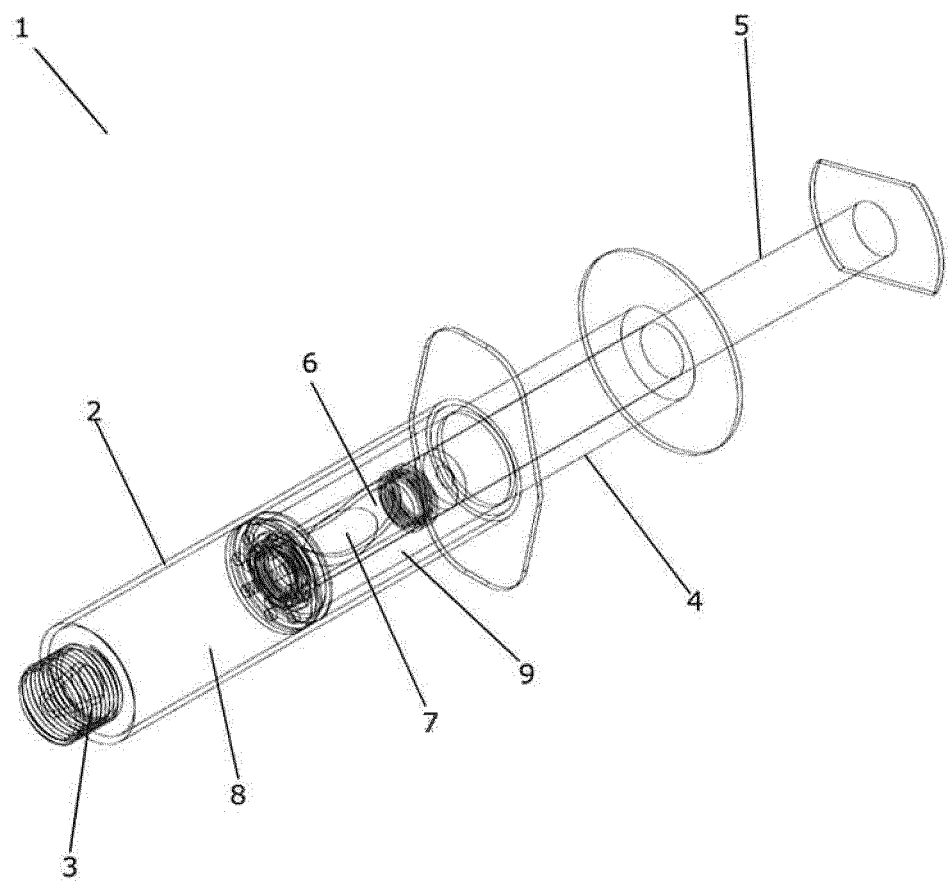
FIG. 2 is a perspective view of the syringe of FIG. 1, FIGS. 3-6 are side views of the syringe of FIGS. 1 and 2 in various positions during operation of the syringe.

FIG. 2 is a perspective view of the syringe 1 of FIG. 1 in an assembled state. It is clear from FIG. 2 how the second plunger 5 is arranged inside the first plunger 4 which is arranged inside the syringe body 2. Thereby a first lumen 8 and a second lumen 9 are defined. A diluent (not visible) is arranged in the first lumen 8 and the pellet 7 containing the active pharmaceutical ingredient is arranged in the second lumen 9. Since the first lumen 8 and the second lumen 9 are separated in the situation illustrated in FIG. 2, the active pharmaceutical ingredient is kept separate from the diluent, and it is therefore possible to store the syringe 1 along with the active pharmaceutical ingredient and the diluent as long as the syringe is kept in the position shown in FIG. 2.

Figure 3:
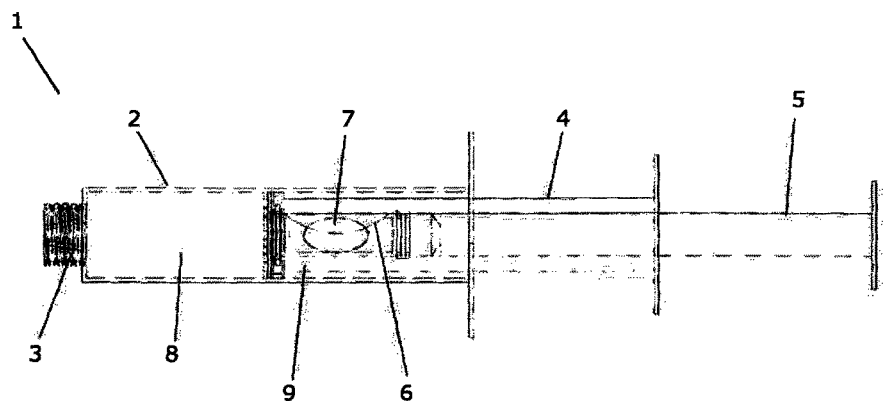

FIG. 3 is a side view of the syringe 1 of FIGS. 1 and 2. In FIG. 3 the syringe 1 is in the same position as in FIG. 2. Thus, FIG. 3 shows the syringe 1 under storage or immediately before use.

Figure 4:
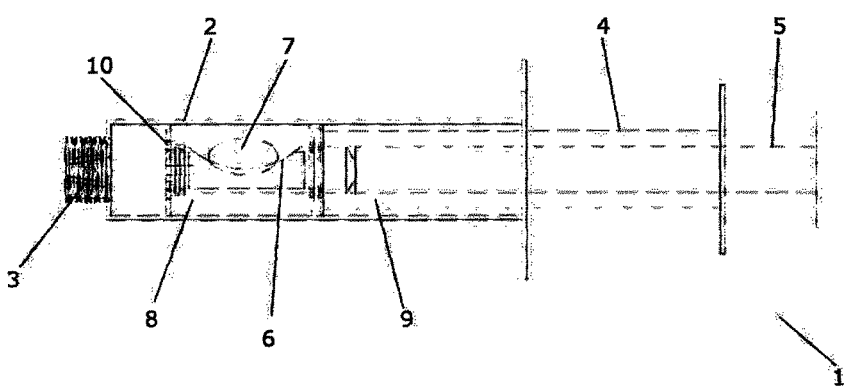

FIG. 4 is a side view of the syringe 1 of FIGS. 1-3. In FIG. 4 the second plunger 5 has been moved towards the threaded end 3 of the syringe body 2. Thereby the cavity 6, and thereby the pellet 7 comprising the active pharmaceutical ingredient, has been moved into the first lumen 8. Accordingly, the active pharmaceutical ingredient is brought into contact with the diluent, i.e. mixing of the active pharmaceutical ingredient and the diluent is commenced. A plate 10 mounted on the second plunger 5 is provided with holes which allow the second plunger 5 to be moved back and forth inside the first lumen 8. This creates turbulence in the diluent, thereby ensuring that the active pharmaceutical ingredient is properly mixed with the diluent.

Figure 5:
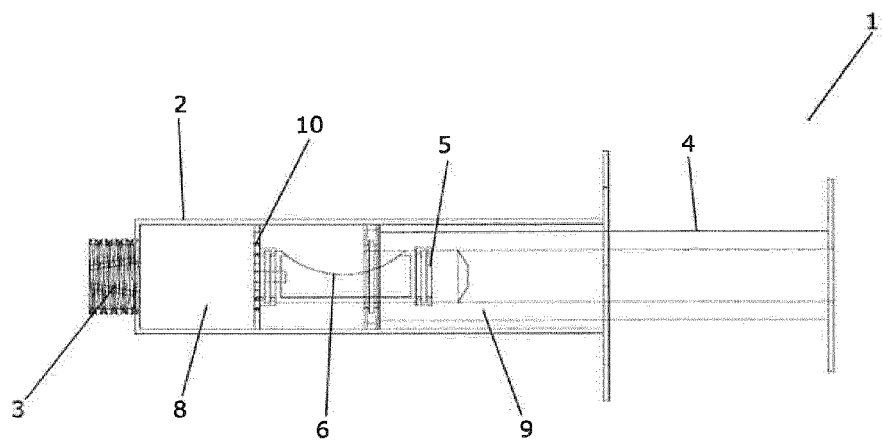

FIG. 5 is a side view of the syringe 1 of FIGS. 1-4. In FIG. 5 the pellet has been completely resolved, i.e. the first lumen 8 contains a mixture of the active pharmaceutical ingredient and the diluent. A part of the second plunger 5 has been broken off in order to allow the operator to push the second plunger 4 towards the threaded end 3.

Figure 6:
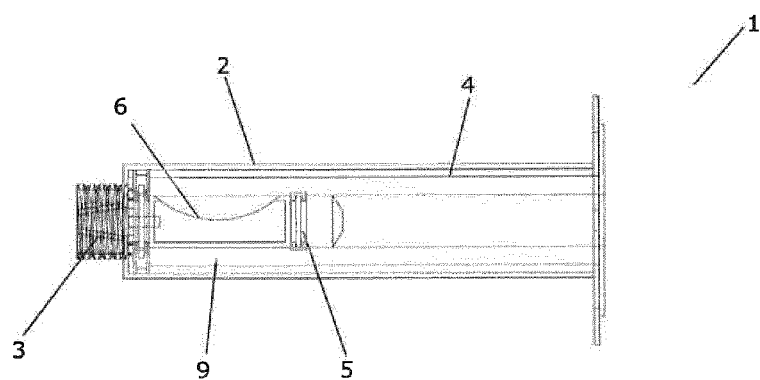

FIG. 6 is a side view of the syringe 1 of FIGS. 1-5. In FIG. 6 the first plunger 4 has been pushed as far as possible in the direction towards the threaded end 3. Thereby the mixture of active pharmaceutical ingredient and diluent which was present in the first lumen has been ejected from the syringe 1, and the first lumen no longer exists.

Figure 7:
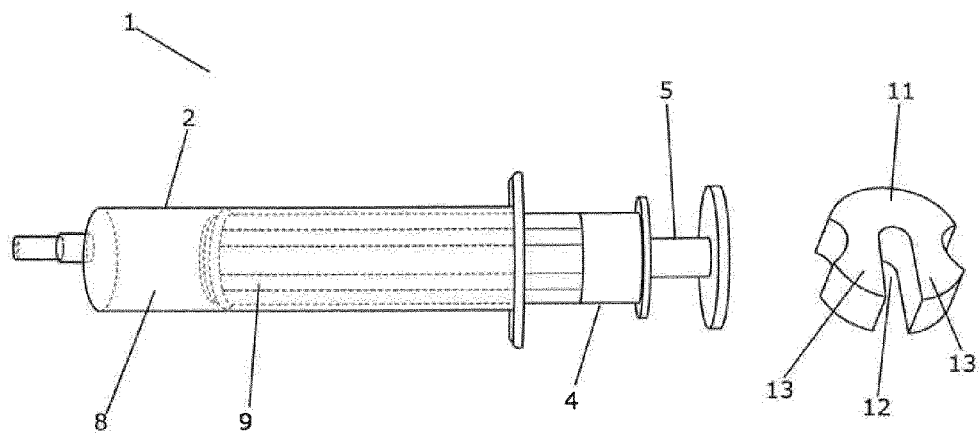
FIG. 7 is a perspective view of a syringe according to a second embodiment of the invention.

FIG. 7 is a perspective view of a syringe 1 according to a second embodiment of the invention. Similarly to the syringe 1 shown in FIGS. 1-6, the syringe 1 of FIG. 7 comprises a syringe body 2, a first plunger 4 and a second plunger 5 arranged coaxially in such a manner that a first lumen 8 is defined by the syringe body 2 and the first plunger 4, and a second lumen 9 is defined by the first plunger 4 and the second plunger 5.

In the syringe 1 of FIG. 7 a liquid diluent may be contained in the first lumen 8, while an active pharmaceutical ingredient, e.g. in dry form, is contained in the second lumen 9, e.g. carried by the second plunger 5 in the manner described above with reference to FIGS. 1-6. Alternatively, a liquid diluent may be contained in the second lumen 9, while an active pharmaceutical ingredient is contained in the first lumen 8. In any event, pushing the second plunger 5 in a forwards direction, i.e. towards the left in FIG. 7, will cause the liquid diluent and the active pharmaceutical ingredient to be brought together in the first lumen 8 or in the second lumen 9. Thereby the diluent and the active pharmaceutical ingredient are mixed, and a diluted active pharmaceutical ingredient is formed. The diluted active pharmaceutical ingredient can then be ejected from the syringe 1 by pushing the first plunger 4 in a forwards direction, i.e. towards the left in FIG. 7.

The syringe 1 of FIG. 7 comprises a detachable locking member 11 being provided with a recess 12 and two pliable legs 13. The recess 12 is arranged to receive a part of the second plunger 5, and is thereby mountable on the syringe 1. The recess 12 may be shaped in such a manner that it has an enlarged diameter in a region arranged near a centre part of the locking member 11. The enlarged diameter may advantageously match the diameter of the part of the second plunger 5 which is to be received in the recess 12. In this case the pliable legs 13 are forced outwards, i.e. in a direction away from each other, when the locking member 11 is being mounted on or removed from the syringe 1. When the locking member 11 is in the correct mounted position, the pliable legs 13 snatch back in their unstrained position, thereby preventing the locking member 11 from accidentally becoming detached from the syringe 1.

In FIG. 7 the locking member 11 is shown detached from the syringe 1.

Figure 8:
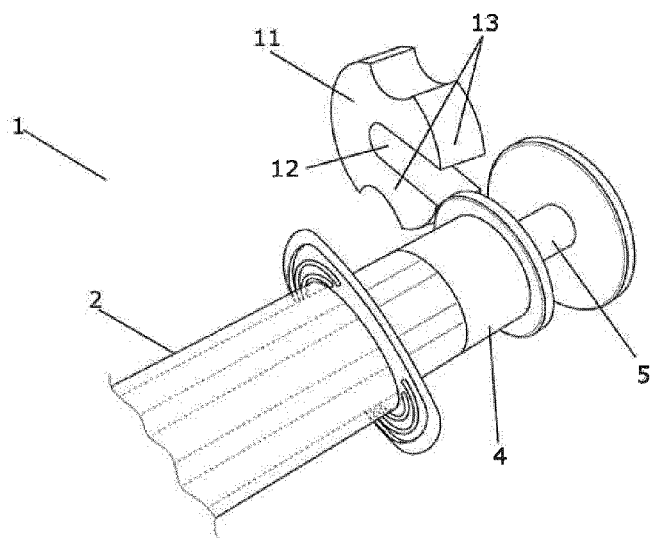
FIGS. 8-10 show details of the syringe of FIG. 7.
Figure 9:
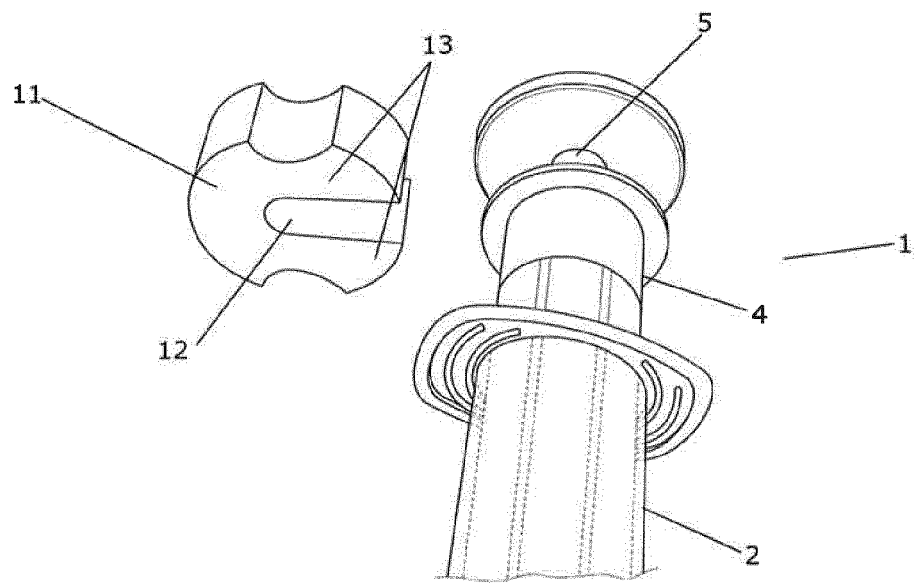

FIGS. 8 and 9 are perspective views of a detail of the syringe 1 of FIG. 7, seen from two different angles. In FIGS. 8 and 9 the locking member 11 is arranged adjacent to the second plunger 5, and is about to be mounted on the second plunger 5.

When the locking member 11 is detached from the syringe 1, as shown in FIGS. 7-9, the second plunger 5 can be moved freely relative to the first plunger 4. Thereby it is possible to operate the second plunger 5 in such a manner that the liquid diluent and the active pharmaceutical ingredient are brought together when the locking member 11 is in this detached position.

Figure 10:
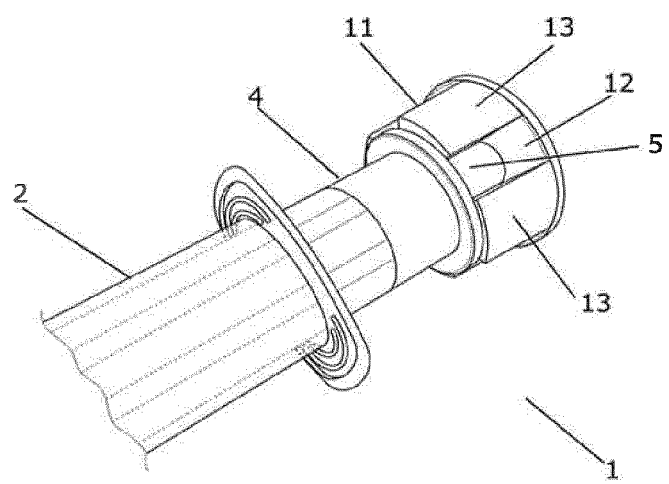

FIG. 10 is a perspective view of the syringe 1 of FIGS. 7-9. In FIG. 10 the locking member 11 is mounted on the second plunger 5 in the manner described above. The locking member 11 prevents the second plunger 5 from moving further in a forwards direction relative to the first plunger 4. Accordingly, when the plungers 4, 5 are pushed, they are moved together, and thereby diluted active pharmaceutical ingredient contained in the first lumen 8 is ejected from the syringe 1.

The syringe 1 of FIGS. 7-10 is preferably operated in the following manner. During storage the locking member 11 is mounted on the syringe 1 in the manner shown in FIG. 10. Thereby it is prevented that the second plunger 5 is accidentally moved relative to the first plunger 4, thereby bringing the liquid diluent and the active pharmaceutical ingredient together, during storage, i.e. it is ensured that the liquid diluent and the active pharmaceutical ingredient are kept separated during storage. When it is desired to mix and eject the active pharmaceutical ingredient, a user breaks the package and removes the locking member 11. As described above, this allows the second plunger 5 to move relative to the first plunger 4.

The user then operates the second plunger 5 in such a manner that the liquid diluent and the active pharmaceutical ingredient are brought together. This may, e.g., be done in the manner described above with reference to FIGS. 3-6.

When the liquid diluent and the active pharmaceutical ingredient have been properly mixed, the locking member 11 is once again mounted on the second plunger 5. As described above, further movements of the second plunger 5 relative to the first plunger 4 are thereby prevented. Then the user pushes the first plunger 4 and the second plunger 5. Since the locking member 11 is in the position shown in FIG. 10, the second plunger 5 moves along with the first plunger 4, and the first plunger 4 moves relative to the syringe body 2, thereby causing the diluted active pharmaceutical ingredient to be ejected from the syringe 1.

Figure 11:
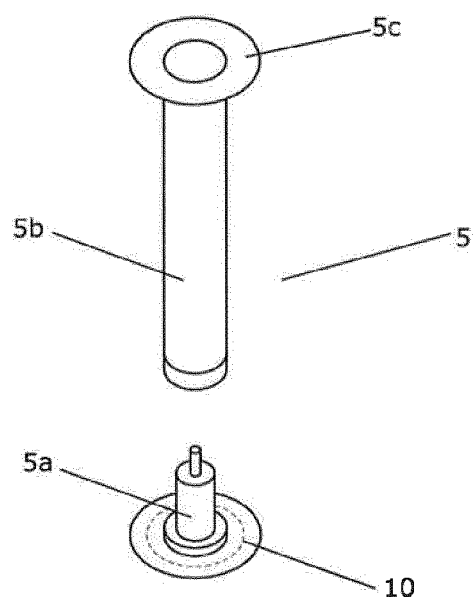
FIG. 11 is a perspective view of a second plunger of a syringe according to a third embodiment of the invention.

FIG. 11 is a perspective view of a second plunger 5 for a syringe according to a third embodiment of the invention. The second plunger 5 comprises a first part 5a and a second part 5b. The first part 5a is adapted to carry an active pharmaceutical ingredient. This will be described in further detail below. A plate 10 provided with holes is mounted on the first part 5a. The plate 10 serves the same purpose as the plate 10 shown in FIGS. 2-4.

The second part 5b comprises a portion 5c which can be manipulated by a user operating the syringe. Thus, pushing the portion 5c moves the second plunger 5 in a forwards direction, and pulling the portion 5c moves the second plunger 5 in a backwards direction.

The first portion 5a has a cross sectional diameter which is smaller than the cross sectional diameter of the second portion 5b. This allows active pharmaceutical ingredient to be accommodated in a region corresponding to the position of the first portion 5a. This will be described in further detail below.

Figure 12:
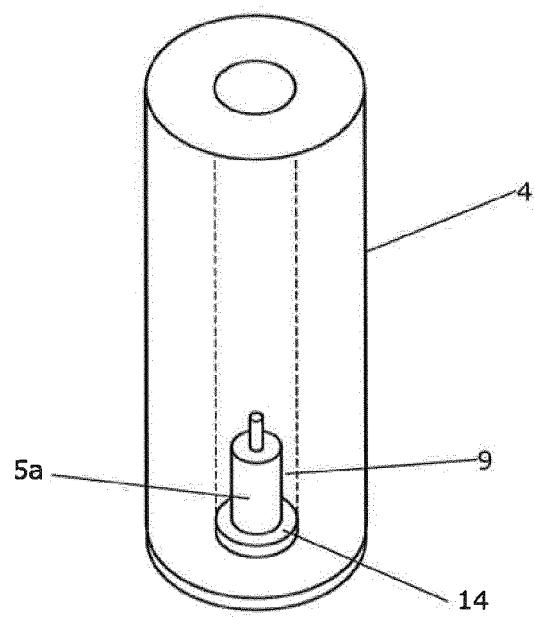
FIG. 12 is a perspective view of a first plunger of a syringe according to the third embodiment of the invention.

In FIG. 11 the first part 5a and the second part 5b are shown detached from each other. This is to illustrate that the first part 5a and the second part 5b are manufactured as two separate parts, and that the two parts 5a, 5b are subsequently attached to each other during assembly of the syringe. FIG. 12 is a perspective view of a first plunger 4 for a syringe according to the third embodiment of the invention. The first part 5a of the second plunger shown in FIG. 11 is mounted in a second lumen 9 inside the first plunger 4. It is clear from FIG. 12 that space is available between the first part 5a of the second plunger and an inner wall of the first plunger 4. Thereby a second lumen 9 is formed. An active pharmaceutical ingredient can be lyophilized directly onto the first part 5a of the second plunger, in the second lumen 9, for instance directly onto surface 14. This may, e.g., be done using normal lyophilisation equipment. Thus, the active pharmaceutical ingredient is arranged in a region corresponding to the position of the small cross sectional diameter of the first part 5a of the second plunger.

The second part of the second plunger may subsequently be attached to the first part 5a of the second plunger, during assembly of the syringe.

Figure 13:
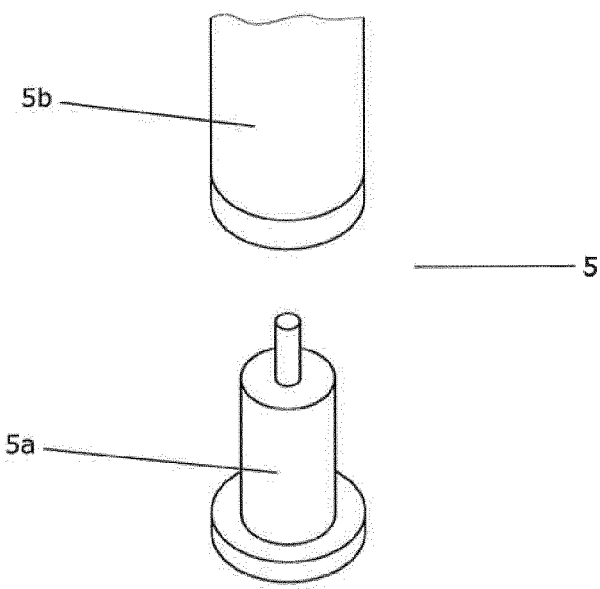
FIG. 13 is a detail of the second plunger of FIG. 11.

FIG. 13 is a detail of the second plunger 5 of FIG. 11. It can be seen that the interface between the first part 5a and the second part 5b of the second plunger 5 is arranged substantially perpendicularly to an axial direction defined by the second plunger 5.

Figure 14:
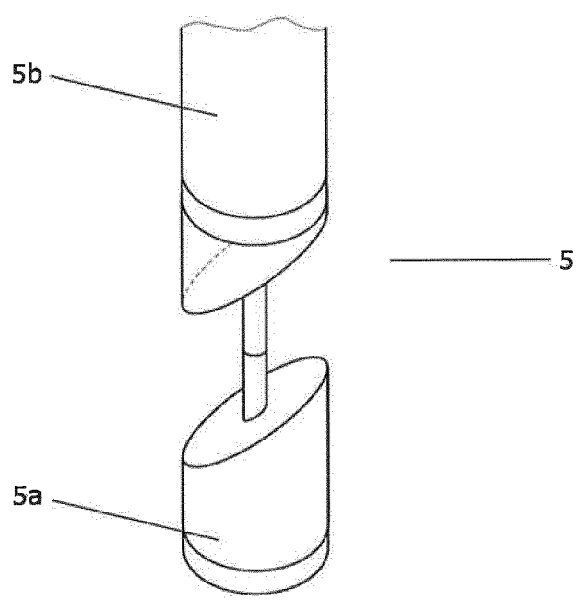
FIG. 14 is a detail of a second plunger according to a fourth embodiment of the invention.

FIG. 14 is a detail of a second plunger 5 for a syringe according to a fourth embodiment of the invention. The syringe according to the fourth embodiment of the invention is very similar to the syringe according to the third embodiment of the invention, in the sense that the second plunger 5 comprises a first part 5a and a second part 5b which are manufactured as separate parts and subsequently attached to each other during assembly of the syringe.

However, in the embodiment shown in FIG. 14, the interface between the first part 5a and the second part 5b is not arranged substantially perpendicularly to an axial direction defined by the second plunger 5. Instead, the interface between the first part 5a and the second part 5b is arranged at approximately 45° with respect to the axial direction.

In the case that a relatively large amount of lyophilized active pharmaceutical ingredient is required in the syringe, there is a risk that part of the active pharmaceutical ingredient is accidentally arranged in small cavities in the second lumen during the lyophilisation process, when the first part 5a of the second plunger has an interface towards the second part of the second plunger which is substantially perpendicular to the axial direction defined by the second plunger, i.e. the situation shown in FIG. 13. This introduces the risk that not all of the active pharmaceutical ingredient is mixed with the liquid diluent during the mixing process taking place in the syringe, and thereby the dose ejected from the syringe is inaccurate and lower than expected.

However, by arranging the interface between the first part 5a and the second part 5b at an angle relative to the axial direction, i.e. as shown in FIG. 14, it is ensured that the liquid containing the active pharmaceutical ingredient is led towards the lower part of the second lumen before the lyophilisation process is commenced. Thereby it is prevented that active pharmaceutical ingredient is accidentally arranged in small cavities in the second lumen, and it is ensured that all of the active pharmaceutical ingredient is mixed with liquid diluent and ejected by the syringe. It should be noted, that even though the interface between the first part 5a and the second part 5b is shown at an angle of approximately 45° with respect to the axial direction, other angles could be envisaged, as long as a slope is defined which leads the liquid towards the lower part of the second lumen. Other shapes could also be used, such as matching conical surfaces.

It should be noted, that even though FIGS. 13 and 14 show the first part 5a and the second part 5b of the second plunger 5 arranged substantially coaxially, it is not ruled out that the first part 5a and the second part 5b could be arranged eccentrically relative to each other.

The invention claimed is:
1. A syringe comprising:
a syringe body defining a first lumen,
a first plunger arranged movably in said first lumen, said first plunger being hollow, thereby defining a second lumen being separated from the first lumen, and
a second plunger arranged movably in said second lumen, wherein a liquid diluent is contained in one of the first lumen and the second lumen, and an active pharmaceutical ingredient is contained in the other of the first lumen and the second lumen, wherein the second plunger is movable in such a manner that the active pharmaceutical ingredient and the liquid diluent are brought together, thereby causing the active pharmaceutical ingredient to be diluted by the diluent, and wherein the first plunger and/or the second plunger is/are movable in such a manner that diluted active pharmaceutical ingredient can be ejected from the syringe, and wherein the second plunger comprises a first part adapted to carry the active pharmaceutical ingredient, and a second part comprising a portion being operable by a user, where the first part and the second part are manufactured as separate parts and attached to each other during assembly of the syringe, and the second part having a cross sectional diameter which is larger than a cross sectional diameter of the first part in an interface region where the first part of the second plunger and the second part of the second plunger are assembled.

2. A syringe according to claim 1, wherein the second plunger is movable in such a manner that the active pharmaceutical ingredient or the liquid diluent carried by the second plunger is moved into the first lumen.

3. A syringe according to claim 1, wherein the second plunger is movable in such a manner that the active pharmaceutical ingredient and the liquid diluent are brought together in the first lumen.

4. A syringe according to claim 1, wherein the syringe body, the first plunger and the second plunger are arranged substantially coaxially.

5. A syringe according to claim 1, wherein at least part of the second plunger can be removed from the syringe.

6. A syringe according to claim 1, further comprising a removable locking member, said locking member being adapted to prevent movements of the second plunger relative to the first plunger when the locking member is mounted on the syringe, and wherein the second plunger is allowed to perform movements relative to the first plunger when the locking member is removed from the syringe.

7. A syringe according to claim 1, wherein a perforated disk is mounted on the second plunger, said perforated disk being arranged in the first lumen in such a manner that a part of the second plunger is allowed to be moved back and forth inside the first lumen.

8. A syringe according to claim 1, wherein the active pharmaceutical ingredient is in a dry form prior to bringing the active pharmaceutical ingredient and the liquid diluent together.

9. A syringe according to claim 1, wherein the active pharmaceutical ingredient is in the form of a solution or a suspension prior to bringing the active pharmaceutical ingredient and the liquid diluent together.

10. A syringe according to claim 9, wherein the diluent is in the form of self-emulsifying oil.

11. A syringe according to claim 1, wherein at least a part of the second plunger is deformable.

12. A syringe according to claim 1, wherein the first part defines a distal end of the second plunger.

13. A syringe according to claim 1, wherein the second plunger further comprises a flange defined at an end of the second part opposite the first part, and the flange having a cross sectional flange diameter which is larger than the cross sectional diameter of the second part.

14. A method for mixing and ejecting an active pharmaceutical ingredient from a syringe, the syringe comprising a syringe body, a first plunger arranged movably inside a first lumen defined by the syringe body and a second plunger arranged movably inside a second lumen defined by the first plunger, a liquid diluent being contained in one of the first lumen and the second lumen, and an active pharmaceutical ingredient being contained in the other of the first lumen and the second lumen, the second plunger comprising a first part adapted to carry the active pharmaceutical ingredient, and the second part comprising a portion being operable by a user, wherein the first part and the second part are manufactured as separate parts and attached to each other during assembly of the syringe, and the second part having a cross sectional diameter which is larger than a cross sectional diameter of the first part in an interface region where the first part of the second plunger and the second part of the second plunger are assembled, the method comprising the steps of:

moving the second plunger, thereby bringing the active pharmaceutical ingredient and the liquid diluent together, mixing the active pharmaceutical ingredient and the liquid diluent, thereby obtaining a diluted active pharmaceutical ingredient, and moving the first plunger and/or the second plunger in such a manner that the diluted active pharmaceutical ingredient is ejected from the syringe.

15. A method according to claim 14, wherein the second plunger further comprises a flange defined at an end of the second part opposite the first part, and the flange having a cross sectional flange diameter which is larger than the cross sectional diameter of the second part.

16. A method according to claim 14, wherein the first part of the second plunger defines a distal end of the second plunger.

17. A method according to claim 16, wherein the step of moving the second plunger brings the active pharmaceutical ingredient and the liquid diluent together in the first lumen, and wherein the step of mixing the active pharmaceutical ingredient and the liquid diluent comprises moving the second plunger back and forth inside the first lumen.

18. A method according to claim 16, further comprising the step of locking the second plunger against movements relative to the first plunger, the said step of locking the second plunger against movements relative to the first plunger being performed after the step of mixing the active pharmaceutical ingredient and the liquid diluent and before the step of moving the first plunger and/or the second plunger.

19. A method according to claim 18, wherein the step of locking the second plunger is performed by mounting a locking member on the syringe.

20. A method according to claim 19, wherein the locking member is mounted on the syringe during storage, and wherein the method further comprises the step of removing the locking member prior to moving the second plunger.

* * * * *

UNITED STATES PATENT AND TRADEMARK OFFICE
CERTIFICATE OF CORRECTION

PATENT NO. : 9,937,295 B2
APPLICATION NO. : 13/982844
DATED : April 10, 2018
INVENTOR(S) : Bar-Shalom Page 1 of 1

It is certified that error appears in the above-identified patent and that said Letters Patent is hereby corrected as shown below:

In the Claims

Column 11,
Line 16, Claim 1 "where the first part" should read --wherein the first part--;
Line 34, Claim 4 "substantially coaxially" should read --coaxially--.

Column 12,
Line 16, Claim 14 "the second part" should read --a second part--;
Lines 41 and 47, Claims 17 and 18 "claim 16", both occurrences, should read --claim 14--;
Line 49, Claim 18 "the said step" should read --the step--.

Signed and Sealed this
Sixteenth Day of October, 2018

Andrei Iancu
*Director of the United States Patent and Trademark Office*